| United States Patent [19] | [11] Patent Number: 4,897,262 |
| --- | --- |
| Nandagiri et al. | [45] Date of Patent: Jan. 30, 1990 |

[54] NON-AEROSOL HAIR SPRAY COMPOSITION

[75] Inventors: Arun Nandagiri, Rockaway; Paul S. Wallace, Glen Rock; Beverly J. Lajoie, River Edge, all of N.J.

[73] Assignee: Playtex Jhirmack, Inc., Stamford, Conn.

[21] Appl. No.: 171,635

[22] Filed: Mar. 22, 1988

[51] Int. Cl.$^4$ ............................................... A61K 7/11
[52] U.S. Cl. ........................................ 424/71; 424/78; 424/DIG. 2
[58] Field of Search ...................... 424/71, 78, DIG. 2

[56] References Cited

U.S. PATENT DOCUMENTS

| 2,995,278 | 8/1961 | Clapp | 222/394 |
| --- | --- | --- | --- |
| 3,850,178 | 11/1974 | Schoenholz | 424/78 X |
| 4,001,392 | 1/1977 | Curry et al. | 424/70 X |
| 4,007,005 | 2/1977 | Patel | 424/DIG. 2 |
| 4,036,291 | 7/1977 | Karg et al. | 424/DIG. 2 |
| 4,044,121 | 8/1977 | Ko | 424/71 |
| 4,164,562 | 8/1979 | Nandagiri et al. | 424/47 |
| 4,165,367 | 8/1979 | Chakrabarti | 424/47 |
| 4,261,972 | 4/1981 | Nandagiri et al. | 424/47 |
| 4,263,275 | 4/1981 | Nandagiri et al. | 424/47 |
| 4,315,910 | 2/1982 | Nowak, Jr. et al. | 424/47 |
| 4,520,008 | 5/1985 | Ando et al. | 424/47 |

*Primary Examiner*—Ellis P. Robinson
*Assistant Examiner*—Susan S. Rucker
*Attorney, Agent, or Firm*—Stewart J. Fried

[57] ABSTRACT

A non-aerosol hair spray composition which provides superior hair styling properties while maintaining good hold or style retention contains about 5 to 10 percent of a lower alkyl ester of an alkyl vinyl ether-maleic acid copolymer, from 10 to 15 percent water, about 73 to 85 percent lower aliphatic alcohol, and up to about 2% of adjuvants.

9 Claims, No Drawings

NON-AEROSOL HAIR SPRAY COMPOSITION

BACKGROUND OF THE INVENTION

A large number of aerosol mousses, styling gels and other forms of styling or fixative products have been introduced into the consumer market in recent years in response to increased demand. These products generally perform well in providing the desired benefits, but they are burdened with inherent disadvantages among which is that they are not multifunctional.

Aerosol mousses, for example, are used to aid in styling but, because they are water-based products, are characterized by having poor hair-holding properties and a lack of resistance to moisture and humidity in the same manner as conventional hair sprays. The advantage of the mousse is also the consequence of the fact that it is water based which permits the consumer adequate time to style his or her hair as desired. However, the consumer must often times use an auxiliary product such as a hair spray in order to hold the hair after styling. Additionally, the mousse has to be dispensed into the palm of the hand before being applied to the hair and, therefore, it is messy to use. Similar problems exist with other styling aids such as gels and styling lotions. Like the mousse, the gel and styling lotions do not hold the hair style well under humid conditions and an auxiliary product, such as a hair spray, may be required to accomplish this purpose.

In order to overcome some of the foregoing problems, and also for the purpose of avoiding the purchase of multiple products, some people have used the available non-aerosol hair sprays both as a styling aid and also as a finishing spray after styling has been completed in order to hold the hair in place. The drawback of these non-aerosol hair sprays, however, is that they dry too quickly and permit the user only a short, and usually inadequate, quantity of time within which to perform the desired styling of the hair, especially when using hot styling implements such as, for instance, a curling iron or hair dryer. The reason that these hair sprays dry so quickly is that they are formulated with 190 proof alcohol having a low water content. The rate of drying can be retarded by increasing the water content, but the ability of these preparations to hold the hair in place decreases as the concentration of water is increased. Thus, hair spray formulations available to date have acted either to permit the user to style his or her hair or to hold his or her hair, but not to accomplish both objectives.

A hair spray formulation has now been discovered which exhibits the dual properties of styling and holding in a single formulation. It has been found that the principal ingredients in the hair spray and their concentration, particularly water, are critical. Within a relatively narrow range of concentrations, the formulation permits the user to optimize the functions of styling the hair and holding the hair in place. Outside of this range, the ability of the composition to either style the hair or hold the hair in place in or for a reasonable amount of time is less than optimal.

The use of water in a hair setting or hair holding formulation is not new. For example, U.S. Pat. No. 4,165,367 describes a hair setting and conditioning composition containing 0.1 to 35 percent of a vinyl pyrrolidone-dialkylaminoalkyl (meth) acrylate copolymer, up to 10 percent of certain cosmetically acceptable adjuvants and a solvent base which can be one or a mixture of water, aliphatic alcohols, trichloroethane or methylene chloride.

A hair setting lotion containing 0.2-10% of a polymer such as lower alkyl esters of methyl vinyl ether and maleic anhydride and an alkylene oxide adduct of a higher alcohol in a solvent such as water, a lower alcohol or both, and containing over 40% propellant is described in U.S. Pat. No. 4,520,008.

Because of shelf life and metal container corrosion considerations, aerosol hair spray resin formulations were initially based on anhydrous alcohol systems because the use of water/alcohol mixtures such as, for instance, 95 percent alcohol, had been found to cause an unacceptable rate of corrosion in uncoated metal containers. To overcome these problems, U.S. Pat. No. 4,315,910 proposes a special composition containing at least one carboxylated or non-ionic hair spray resin, 1 to 15 percent water, a propellant which is either 2 to 7 percent carbon dioxide or 5 to 35 percent hydrocarbon or a mixture thereof with the remainder of the composition being ethanol or isopropanol, or a combination of these two alcohols. U.S. Pat. No. 2,995,278 teaches the use of aqueous alcohol solutions together with a halogenated hydrocarbon/hydrocarbon propellant system, which formulations remain in two separate phases until mixed and propelled using a specialized mixing chamber and valving device. The water in this formulation is at least 30 percent of the water alcohol mixture and acts to retard flammability, reduce cost and to allow expansion of the available (that is, employable) ingredients.

The propellants originally used in aerosol hair spray formulations were fluorocarbons. These propellants were believed to damage the ozone layer and as a result their use in consumer products has become restricted. Formulators therefore have changed to the use of hydrocarbon propellants such as propane, n-butane, isobutane and mixtures thereof, but these hydrocarbons are highly flammable, making it necessary to include a fire or flame retardant to suppress the flammability of the resulting compositions. Water has been used as a flame retardant in such compositions. For example, U.S. Pat. No. 4,164,562 describes formulations containing 2 to 12 percent water to reduce flammability of the composition. The polymer used in this hair spray composition is a copolymer of methyl vinyl ether and monoethyl or monobutyl ester of maleic acid in which at least 10 percent of the free carboxyl groups are neutralized with an organic base such as, for example, ammonia, dimethyl-, di- and tri-ethyl, and triisopropyl amine, and 2-methyl-2-amino-1-propanol. A similar composition additionally containing a quaternary ammonium polyethoxylated phosphate is described in U.S. Pat. No. 4,263,275. U.S. Pat. No. 4,261,972 describes a similar composition in which the resin has been changed to an acrylic and/or methacrylic resin which permits larger quantities of water to be used in order to help restore the moisture content of the hair which may be lost by the use of blow dryers and hot combs. These compositions contain 2 to 30 percent water, preferably 25 percent water.

It is the object of this invention to provide new non-aerosol hair spray compositions which provide superior hair styling properties while maintaining good hold or style retention properties. This and other objects of the invention will become apparent to those of ordinary skill in this art from the following detailed description.

SUMMARY OF THE INVENTION

The present invention relates to a nonaerosol hair spray composition which provides both superior hair styling properties and good holding and style retention characteristics. More particularly, the non-aerosol hair spray composition contains about 5 to 10 percent lower alkyl ester of alkyl vinyl ethermaleic acid copolymer, about 10 to 15 percent water, about 73 to 85 percent aliphatic alcohol and up to about 2 percent adjuvants and, when applied to the hair, permits the user to style the hair and then maintain that style.

DETAILED DESCRIPTION OF THE INVENTION

The present invention provides a composition consisting essentially of about 5 to 10 percent of a resin which is a lower alkyl ester of alkyl vinyl ether-maleic acid copolymer, about 10 to 15 percent water, about 73 to 85 percent aliphatic 2 to 3 carbon atom alcohol and up to about 2 percent adjuvants. The hair spray formulation does not contain any aerosol propellant. It may be dispensed from any conventional non-aerosol preparation spray container, such as for example a pump spray.

The resin used in this invention is a copolymer of a lower alkyl ester, i.e., a 1 to 4 carbon atom alkyl ester, of alkyl vinyl ether-maleic acid copolymer. The copolymer thus has a repeating unit represented by the formula

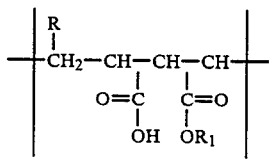

wherein R and $R_1$ are alkyl radicals containing one to four carbon atoms. $R_1$ is preferably ethyl or butyl and is most preferably ethyl.

Among the vinyl alkyl ethers useful in preparing the resins may be mentioned methyl vinyl ether and butyl vinyl ether. Of these, the methyl vinyl ether is preferred. These resins are well known commodities of commerce and generally have molecular weights in the range of 15,000 to 60,000 and a viscosity between about 1.5 and 6 centipoises when measured as a 5 percent solution in dimethylformamide at 34° C. The monoethyl ester of methyl vinyl ether-maleic acid copolymer is commercially available as Gantrez ES-225 and the butyl monoester of the methyl vinyl ether-maleic a id copolymer is commercially available as Gantrez ES-425, both of these products being available commercially as 50 percent solutions in ethanol or isopropanol. The polymers are not water-soluble. The resin is preferably neutralized to the extent of about 10 to 25 percent of the free carboxyl group by the addition of an organic base, e.g. 2-methyl-2-amino-1-propanol, dimethyl- or diethylamine, triethanol- or triisopropanol amine, ammonia and the like. Preferably, the resin in the non-aerosol hair spray formulation of the present invention is employed in an amount of about 7.5 to 9 percent based on the total weight of the composition.

The alcohol employed in the composition is an aliphatic, 2 to 3 carbon atom, monohydric alcohol. Isopropanol and especially ethanol are preferred. The concentration of the alcohol in the composition is preferably about 77 to 80 percent. The concentration of the water in the composition is preferably about 11.5 to 13 percent.

The formulations of the present invention can contain the conventional hair spray adjuvants in amounts which generally range from about 0.1 to 2 percent by weight and preferably about 0.75 to 1 percent by weight. Among the additives which can be used are plasticizers such as glycols, pthalate esters and glycerine; silicones; emollients; lubricants and penetrants such as various lanolin compounds; protein hydrolysates and other protein derivatives; ethylene adducts and polyoxyethylene cholesterol; dyes, tints and other colorants; and perfumes.

In order to demonstrate the necessity of maintaining the concentration values heretofore recited, three formulations of non-aerosol hair spray were prepared. The formulations were as follows:

| Ingredient | Percent by Weight in | | |
| --- | --- | --- | --- |
| | Formulation I | Formulation II | Formulation III |
| Anhydrous Ethanol | 83.245 | 78.305 | 68.305 |
| 2-Amino-2-Methyl-1-Propanol | 0.180 | 0.18 | 0.18 |
| Monoethyl Ester of Methyl Vinyl Ether-Maleic Acid Copolymer | 8.350 | 8.35 | 8.35 |
| Water | 7.400 | 12.34 | 22.34 |
| Panthenol | 0.500 | 0.50 | 0.50 |
| Quaternium-26 | 0.100 | 0.10 | 0.10 |
| Dimethicone Copolyol | 0.100 | 0.10 | 0.10 |
| Fragrance | 0.125 | 0.125 | 0.125 |

The hair holding properties of the three formulations were evaluated pursuant to the standard Humidity Curl Retention test described on page 432 of "The Aerosol Handbood" by Montfort A. Johnsen, 2nd Edition, Wayne Dorland Co.

The following results were obtained:

| Formulations | Time in Hours | | | | | | |
| --- | --- | --- | --- | --- | --- | --- | --- |
| | ¼ | ½ | 1.0 | 1.5 | 2.0 | 3.0 | 4.0 |
| I | 78% | 73% | 70% | 69% | 68% | 66% | 64% |
| II | 90% | 87% | 85% | 85% | 84% | 82% | 81% |
| III | 90% | 87% | 86% | 85% | 83% | 82% | 82% |

The foregoing data shows that the percent curl retention of Formulation II was significantly better than that of Formulation I at each of the time intervals. It is believed that the high alcohol content Formulation I, when sprayed on the hair, dries the hair and then, when placed in the humidity chamber, rapidly picks up the lost moisture, causing the curls to droop in the high humidity environment. In the low alcohol-high water content Formulation III, the curl retention results were good but the hair took a significantly longer time to dry and exhibited a longer period of tackiness, which is undesirable. The following table sets forth the results of twelve evaluations in which the Formulations were applied to hair and the amount of time necessary to eliminate the tacky and wet feeling was noted:

| | I | II | III |
| --- | --- | --- | --- |
| No Tack Time, sec. | 28 | 52 | 72 |

| -continued | | | |
|---|---|---|---|
| | I | II | III |
| Drying Time, sec. | 54 | 72 | 94 |

The water content of Formulation II does not drive out the natural moisture in the hair or disrupt the hydrogen bonding of the hair once the hair is set in the desired configuration and also does not require the passage of an inordinate amount of time for the hair to dry.

It will be appreciated that various changes can be made in the composition of the present non-aerosol hair spray formulation and in its use without departing from the spirit and scope of the present invention. The various embodiments which have been described herein were intended to further illustrate the invention, but were not intended to limit it.

What is claimed is:

1. A non-aerosol hair spray for styling and holding the hair consisting essentially by weight of about 5 to 10 percent of a partly neutralized alkyl ester of alkyl vinyl ether maleic acid copolymer, in which the alkyl ester consists of four carbons or less, about 10 to 15 percent water, about 73 to 85 percent aliphatic 2 to 3 carbon atom monohydric alcohol and about 0.1 to 2 percent adjuvant.

2. The non-aerosol hair spray composition of claim 1, in which the lower alkyl ester is partly neutralized monoethyl or monobutyl ester of methyl vinyl ether-maleic acid copolymer and the alcohol is ethanol or isopropanol.

3. The non-aerosol hair spray composition of claim 2, in which the amount of resin is about 7.5 to 9 percent, the amount of water is about 11.5 to 13 percent, the amount of alcohol is about 77 to 80 percent and the amount of adjuvant is about 0.75 to 1 percent.

4. The non-aerosol hair spray composition of claim 3, in which the lower alkyl ester is the ethyl ester and the alcohol is ethanol.

5. The non-aerosol hair spray formulation of claim 4, consisting of the said resin, water, ethanol, panthenol, quaternium-26, and dimethicone copolyol.

6. The non-aerosol hair spray formulation of claim 5, in which the ethanol is about 78 percent, the water is about 12 percent and the resin is about 8percent.

7. In a method of applying a composition to the hair to style and hold the hair, the improvement which comprises employing the non-aerosol of hair spray of claim 1 as said composition whereby a single composition permits the user to suquentially both style and hold the hair.

8. In a method of applying a composition to the hair to style and hold the hair, the improvement which comprises employing the non-aerosol of hair spray of claim 3 as said composition whereby a single composition permits the user to sequentially both style and hold the hair.

9. In a method of applying a composition to the hair to style and hold the hair, the improvement which comprises employing the non-aerosol of hair spray of claim 5 as said composition whereby a single composition permits the user to sequentially both style and hold the hair.

* * * * *